(12) United States Patent (10) Patent No.: US 7,896,885 B2
Miniaci et al. (45) Date of Patent: Mar. 1, 2011

(54) RETROGRADE DELIVERY OF RESURFACING DEVICES

(75) Inventors: Anthony Miniaci, Bentleyville, OH (US); Steven W. Ek, Bolton, MA (US)

(73) Assignee: Arthrosurface Inc., Franklin, MA (US)

( * ) Notice: Subject to any disclaimer, the term of this patent is extended or adjusted under 35 U.S.C. 154(b) by 80 days.

(21) Appl. No.: 10/994,453

(22) Filed: Nov. 22, 2004

(65) Prior Publication Data

US 2005/0154398 A1 Jul. 14, 2005

Related U.S. Application Data

(63) Continuation-in-part of application No. 10/308,718, filed on Dec. 3, 2002, now Pat. No. 7,163,541.

(60) Provisional application No. 60/523,810, filed on Nov. 20, 2003.

(51) Int. Cl.
*A61B 17/90* (2006.01)
(52) U.S. Cl. ............................................. 606/96; 606/80
(58) Field of Classification Search .................. 606/79, 606/80, 86–89, 96–99, 103, 104
See application file for complete search history.

(56) References Cited

U.S. PATENT DOCUMENTS

| 992,819 | A | 5/1911 | Springer |
| 1,451,610 | A | 4/1923 | Gestas |
| 2,267,925 | A | 12/1941 | Johnston |
| 2,570,465 | A | 10/1951 | Lundholm |
| 3,176,395 | A | 4/1965 | Warner et al. |
| 3,840,905 | A | 10/1974 | Deane |
| 4,016,651 | A | 4/1977 | Kawahara et al. |
| 4,034,418 | A | 7/1977 | Jackson et al. |
| 4,044,464 | A | 8/1977 | Schiess et al. |
| 4,158,894 | A | 6/1979 | Worrell |

(Continued)

FOREIGN PATENT DOCUMENTS

AU 2001262308 12/2001

(Continued)

OTHER PUBLICATIONS

ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).

(Continued)

*Primary Examiner*—Thomas C Barrett
*Assistant Examiner*—Larry E Waggle, Jr.
(74) *Attorney, Agent, or Firm*—Grossman Tucker Perreault & Pfleger PLLC

(57) ABSTRACT

A method according to one embodiment may provide access to an articular surface of a bone. The method includes forming a passage through at least a portion of the bone. The passage provides an opening in the articular surface. The method further includes inserting a tether through the passage. The tether inserted through the passage can be coupled to at least one device from an insertion site remote from the articular surface. The tether can be withdrawn through the passage to convey the device to a location proximate the articular surface.

18 Claims, 5 Drawing Sheets

U.S. PATENT DOCUMENTS

| | | | |
|---|---|---|---|
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A * | 8/1985 | Hourahane et al. | 606/86 R |
| 4,565,768 A * | 1/1986 | Nonogaki et al. | 430/197 |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,712,545 A | 12/1987 | Honkanen | |
| 4,714,478 A | 12/1987 | Fischer | |
| 4,719,908 A | 1/1988 | Averill et al. | |
| 4,729,761 A | 3/1988 | White | |
| 4,781,182 A * | 11/1988 | Purnell et al. | 606/96 |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,927,421 A | 5/1990 | Goble et al. | |
| 4,936,853 A | 6/1990 | Fabian et al. | |
| 4,938,778 A | 7/1990 | Ohyabu et al. | |
| 4,940,467 A | 7/1990 | Tronzo | |
| 4,976,037 A | 12/1990 | Hines | |
| 4,978,258 A | 12/1990 | Lins | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,100,405 A | 3/1992 | McLaren | |
| 5,127,920 A | 7/1992 | MacArthur | |
| 5,192,291 A | 3/1993 | Pannek, Jr. | |
| 5,201,881 A | 4/1993 | Evans | |
| 5,211,647 A | 5/1993 | Schmieding | |
| 5,224,945 A | 7/1993 | Pannek, Jr. | |
| 5,234,435 A * | 8/1993 | Seagrave, Jr. | 606/103 |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,314,478 A | 5/1994 | Oka et al. | |
| 5,314,482 A | 5/1994 | Goodfellow et al. | |
| 5,324,295 A | 6/1994 | Shapiro | |
| 5,336,224 A | 8/1994 | Selman | |
| 5,354,300 A * | 10/1994 | Goble et al. | 606/80 |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A | 4/1995 | Ethridge | |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,601,550 A | 2/1997 | Esser | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A | 6/1997 | Houston et al. | |
| 5,645,598 A | 7/1997 | Brosnahan, III | |
| 5,681,311 A | 10/1997 | Foley et al. | |
| 5,682,886 A | 11/1997 | Delp et al. | |
| 5,683,400 A * | 11/1997 | McGuire | 606/96 |
| 5,683,465 A | 11/1997 | Shinn et al. | |
| 5,683,466 A | 11/1997 | Viatle | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A | 6/1998 | Hirsch et al. | |
| 5,769,855 A | 6/1998 | Bertin et al. | |
| 5,769,899 A | 6/1998 | Schwartz et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,817,095 A | 10/1998 | Smith | |
| 5,824,087 A | 10/1998 | Aspden et al. | |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A | 7/1999 | Mirza | |
| 5,928,286 A | 7/1999 | Ashby et al. | |
| 5,964,752 A | 10/1999 | Stone | |
| 5,964,768 A | 10/1999 | Huebner | |
| 5,964,808 A | 10/1999 | Blaha et al. | |
| 5,968,050 A | 10/1999 | Torrie | |
| 5,989,269 A | 11/1999 | Vibe-Hansen et al. | |
| 5,990,382 A | 11/1999 | Fox | |
| 5,997,543 A | 12/1999 | Truscott | |
| 5,997,582 A | 12/1999 | Weiss | |
| 6,004,323 A | 12/1999 | Park et al. | |
| 6,010,502 A | 1/2000 | Bagby | |
| 6,015,411 A * | 1/2000 | Ohkoshi et al. | 606/80 |
| 6,017,348 A | 1/2000 | Hart et al. | |
| 6,019,767 A | 2/2000 | Howell | |
| 6,045,564 A | 4/2000 | Walen | |
| 6,052,909 A | 4/2000 | Gardner | |
| 6,059,831 A | 5/2000 | Braslow | |
| 6,071,310 A | 6/2000 | Picha et al. | |
| 6,081,741 A | 6/2000 | Hollis | |
| 6,086,593 A | 7/2000 | Bonutti | |
| 6,102,948 A | 8/2000 | Brosnahan, III | |
| 6,120,511 A * | 9/2000 | Chan | 606/96 |
| 6,120,542 A | 9/2000 | Camino et al. | |
| 6,132,433 A | 10/2000 | Whelan | |
| 6,146,385 A | 11/2000 | Torrie et al. | |
| 6,149,654 A | 11/2000 | Johnson | |

| | | | | | | |
|---|---|---|---|---|---|---|
| 6,159,216 | A | 12/2000 | Burkinshaw et al. | 7,311,702 B2 | 12/2007 | Tallarida et al. |
| 6,165,223 | A | 12/2000 | Metzger et al. | 7,510,558 B2 | 3/2009 | Tallarida |
| 6,168,626 | B1 | 1/2001 | Hyon et al. | 7,569,059 B2 | 8/2009 | Cerundolo |
| 6,171,340 | B1 | 1/2001 | McDowell | 7,641,658 B2 | 1/2010 | Shaolian et al. |
| 6,193,724 | B1 | 2/2001 | Chan | 2001/0012967 A1 * | 8/2001 | Mosseri .................. 623/23.12 |
| 6,206,885 | B1 | 3/2001 | Ghahremani et al. | 2001/0039455 A1 | 11/2001 | Simon et al. |
| 6,217,549 | B1 | 4/2001 | Selmon et al. | 2001/0056266 A1 | 12/2001 | Tallarida et al. |
| 6,217,619 | B1 | 4/2001 | Keller | 2002/0055783 A1 | 5/2002 | Tallarida et al. |
| 6,235,060 | B1 | 5/2001 | Kubein-Meesenburg et al. | 2002/0106393 A1 | 8/2002 | Bianchi et al. |
| 6,251,143 | B1 | 6/2001 | Schwartz et al. | 2002/0138150 A1 | 9/2002 | Leclercq |
| 6,280,474 | B1 | 8/2001 | Cassidy et al. | 2002/0143342 A1 * | 10/2002 | Hangody et al. ............... 606/87 |
| 6,299,645 | B1 | 10/2001 | Ogden | 2002/0147498 A1 | 10/2002 | Tallarida et al. |
| 6,299,648 | B1 | 10/2001 | Doubler et al. | 2003/0028196 A1 | 2/2003 | Bonutti |
| 6,306,142 | B1 | 10/2001 | Johanson et al. | 2003/0060887 A1 | 3/2003 | Ek |
| 6,315,798 | B1 | 11/2001 | Ashby et al. | 2003/0065391 A1 | 4/2003 | Re et al. |
| 6,322,500 | B1 | 11/2001 | Sikora et al. | 2003/0105465 A1 | 6/2003 | Schmieding et al. |
| 6,328,752 | B1 | 12/2001 | Sjostrom et al. | 2003/0120276 A1 | 6/2003 | Tallarida et al. |
| 6,342,075 | B1 | 1/2002 | MacArthur | 2003/0120278 A1 | 6/2003 | Morgan et al. |
| 6,358,251 | B1 | 3/2002 | Mirza | 2003/0130741 A1 * | 7/2003 | McMinn .................. 623/23.14 |
| 6,358,253 | B1 | 3/2002 | Torrie et al. | 2003/0171756 A1 | 9/2003 | Fallin et al. |
| 6,375,658 | B1 | 4/2002 | Hangody et al. | 2003/0181878 A1 | 9/2003 | Tallarida et al. |
| 6,383,188 | B2 | 5/2002 | Kuslich | 2003/0204195 A1 | 10/2003 | Keane et al. |
| 6,415,516 | B1 | 7/2002 | Tirado et al. | 2003/0216669 A1 | 11/2003 | Lang et al. |
| 6,443,954 | B1 | 9/2002 | Bramlet et al. | 2003/0225456 A1 | 12/2003 | Ek |
| 6,461,373 | B2 | 10/2002 | Wyman et al. | 2003/0225457 A1 | 12/2003 | Justin et al. |
| 6,468,309 | B1 | 10/2002 | Lieberman | 2003/0229352 A1 * | 12/2003 | Penenberg .................. 606/81 |
| 6,478,801 | B1 | 11/2002 | Ralph et al. | 2004/0015170 A1 | 1/2004 | Tallarida et al. |
| 6,482,210 | B1 | 11/2002 | Skiba et al. | 2004/0034359 A1 | 2/2004 | Schmieding et al. |
| 6,494,914 | B2 | 12/2002 | Brown | 2004/0034437 A1 | 2/2004 | Schmieding |
| 6,520,964 | B2 | 2/2003 | Tallarida et al. | 2004/0082906 A1 | 4/2004 | Tallarida et al. |
| 6,527,754 | B1 | 3/2003 | Tallarida et al. | 2004/0106928 A1 | 6/2004 | Ek |
| 6,530,956 | B1 | 3/2003 | Mansmann | 2004/0133276 A1 | 7/2004 | Lang et al. |
| 6,537,274 | B1 | 3/2003 | Katz | 2004/0138754 A1 | 7/2004 | Lang et al. |
| 6,540,786 | B2 | 4/2003 | Chibrac et al. | 2004/0138758 A1 | 7/2004 | Evans et al. |
| 6,551,322 | B1 | 4/2003 | Lieberman | 2004/0148030 A1 | 7/2004 | Ek |
| 6,575,982 | B1 | 6/2003 | Bonutti | 2004/0153087 A1 | 8/2004 | Sanford et al. |
| 6,585,666 | B2 | 7/2003 | Suh et al. | 2004/0193281 A1 | 9/2004 | Grimes |
| 6,591,581 | B2 | 7/2003 | Schmieding | 2004/0199166 A1 * | 10/2004 | Schmieding et al. .......... 606/79 |
| 6,599,321 | B2 | 7/2003 | Hyde et al. | 2004/0210309 A1 | 10/2004 | Denzer et al. |
| 6,607,561 | B2 | 8/2003 | Brannon | 2004/0230315 A1 | 11/2004 | Ek |
| 6,610,067 | B2 | 8/2003 | Tallarida | 2004/0260303 A1 | 12/2004 | Carrison |
| 6,679,917 | B2 | 1/2004 | Ek | 2005/0015153 A1 | 1/2005 | Goble et al. |
| 6,746,451 | B2 | 6/2004 | Middleton et al. | 2005/0038520 A1 | 2/2005 | Binette et al. |
| 6,755,837 | B2 | 6/2004 | Ebner | 2005/0043805 A1 | 2/2005 | Chudik |
| 6,755,865 | B2 * | 6/2004 | Tarabishy ................ 623/22.12 | 2005/0043808 A1 | 2/2005 | Felt et al. |
| 6,770,078 | B2 | 8/2004 | Bonutti | 2005/0065612 A1 | 3/2005 | Winslow |
| 6,783,550 | B2 | 8/2004 | MacArthur | 2005/0075642 A1 | 4/2005 | Felt |
| 6,783,551 | B1 | 8/2004 | Metzger et al. | 2005/0143731 A1 | 6/2005 | Justin et al. |
| 6,802,864 | B2 | 10/2004 | Tornier | 2005/0143745 A1 | 6/2005 | Hodorek et al. |
| 6,814,735 | B1 | 11/2004 | Zirngibl | 2005/0143831 A1 | 6/2005 | Justin et al. |
| 6,827,722 | B1 | 12/2004 | Schoenefeld | 2005/0209705 A1 | 9/2005 | Niederauer et al. |
| 6,860,902 | B2 | 3/2005 | Reiley | 2005/0229323 A1 | 10/2005 | Mills et al. |
| 6,884,246 | B1 | 4/2005 | Sonnabend et al. | 2005/0287187 A1 | 12/2005 | Mansmann |
| 6,923,813 | B2 | 8/2005 | Phillips et al. | 2006/0004461 A1 | 1/2006 | Justin et al. |
| 6,926,739 | B1 | 8/2005 | OConnor | 2006/0020343 A1 | 1/2006 | Ek |
| 6,962,577 | B2 | 11/2005 | Tallarida et al. | 2006/0052878 A1 | 3/2006 | Schmieding |
| 6,969,393 | B2 | 11/2005 | Pinczewski et al. | 2006/0058744 A1 | 3/2006 | Tallarida et al. |
| 6,989,016 | B2 | 1/2006 | Tallarida et al. | 2006/0058883 A1 | 3/2006 | Aram et al. |
| 7,029,479 | B2 | 4/2006 | Tallarida | 2006/0085006 A1 | 4/2006 | Ek |
| 7,063,717 | B2 | 6/2006 | St. Pierre et al. | 2006/0149370 A1 | 7/2006 | Schmieding et al. |
| 7,115,131 | B2 | 10/2006 | Engh et al. | 2006/0190002 A1 | 8/2006 | Tallarida |
| 7,156,880 | B2 | 1/2007 | Evans et al. | 2006/0195112 A1 | 8/2006 | Ek |
| 7,160,305 | B2 * | 1/2007 | Schmieding .................. 606/80 | 2006/0229726 A1 | 10/2006 | Ek |
| 7,163,541 | B2 | 1/2007 | Ek | 2007/0005143 A1 | 1/2007 | Ek |
| 7,166,133 | B2 | 1/2007 | Evans et al. | 2007/0073394 A1 | 3/2007 | Seedhom et al. |
| 7,192,431 | B2 | 3/2007 | Hangody et al. | 2007/0093842 A1 | 4/2007 | Schmieding |
| 7,204,839 | B2 | 4/2007 | Dreyfuss et al. | 2007/0093890 A1 | 4/2007 | Eliasen et al. |
| 7,204,854 | B2 | 4/2007 | Guederian et al. | 2007/0118136 A1 | 5/2007 | Ek |
| 7,235,107 | B2 | 6/2007 | Evans et al. | 2007/0123921 A1 | 5/2007 | Ek |
| 7,238,189 | B2 * | 7/2007 | Schmieding et al. .......... 606/80 | 2007/0179608 A1 | 8/2007 | Ek |
| 7,241,316 | B2 | 7/2007 | Evans et al. | 2007/0233128 A1 | 10/2007 | Schmieding et al. |
| 7,264,634 | B2 | 9/2007 | Schmieding | 2007/0250067 A1 | 10/2007 | Schmieding et al. |
| 7,303,577 | B1 | 12/2007 | Dean | 2007/0255399 A1 | 11/2007 | Eliasen et al. |

| | | | |
|---|---|---|---|
| 2007/0265700 A1 | 11/2007 | Eliasen et al. | |
| 2007/0288031 A1 | 12/2007 | Dreyfuss et al. | |
| 2007/0299519 A1 | 12/2007 | Schmieding | |
| 2008/0004659 A1 | 1/2008 | Burkhart et al. | |
| 2008/0015709 A1 | 1/2008 | Evans et al. | |
| 2008/0027430 A1 | 1/2008 | Montgomery et al. | |
| 2008/0033443 A1 | 2/2008 | Sikora et al. | |
| 2008/0086139 A1 | 4/2008 | Bourke et al. | |
| 2008/0172125 A1 | 7/2008 | Ek | |
| 2008/0183290 A1 | 7/2008 | Baird et al. | |
| 2008/0188935 A1 | 8/2008 | Saylor et al. | |
| 2008/0275512 A1 | 11/2008 | Albertirio et al. | |
| 2008/0306483 A1 | 12/2008 | Iannarone | |
| 2009/0198288 A1 | 8/2009 | Hoof et al. | |
| 2009/0234452 A1 | 9/2009 | Steiner et al. | |

FOREIGN PATENT DOCUMENTS

| | | |
|---|---|---|
| AU | 2003262428 | 8/2009 |
| DE | 2933174 | 4/1980 |
| DE | 3516743 | 11/1986 |
| DE | 3840466 | 6/1990 |
| EP | 0241240 | 10/1987 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 9920192 | 4/1999 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | WO 02/086180 A2 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 2006004885 | 1/2006 |
| WO | 2006091686 | 8/2006 |

OTHER PUBLICATIONS

PCT International Search Report with written opinion dated Jan. 30, 2006 (6 pgs).
Article—"Arthroscopically Assisted Treatment of Tibial Plateau Fractures", Suganuma, Jun and Akutsu, Seiji, The Journal of Arthroscopic and Related Surgery, vol. 20, No. 10, Dec. 2004, pp. 1084-1089.
EPO Examination Report dated Feb. 22, 2005, in corresponding EPO Application No. 01 932 833.5 (3 pgs).
EPO Office Action dated Mar. 15, 2005, in corresponding EPO Application No. 03 026 286.9 (3 pgs).
EPO Office Action dated Aug. 23, 2004, in related EPO Application No. 03 026 286.9 (4 pgs).
EPO Search Report in related EPO Application No. 03 02 6286.9 dated Apr. 27, 2004 (6 pgs).
M. Siguier, MD et al, "Preliminary Results of Partial Surface Replacement of the Femoral Head in Osteonecrosis", The Journal of Arthroplasty, vol. 14, No. 1, 1999, pp. 45-51.
T. Siguier, MD et al, "Partial Resurfacing Arthroplasty of the Femoral Head in Avascular Necrosis", Clinical Orthopaedics and Related Research, No. 386, 2001, pp. 85-92.
International Search Report with Written Opinion dated Sep. 29, 2006 in corresponding International Patent Application Serial No. PCT/US05/30120 (9 pages).
International Search Report with Written Opinion dated Nov. 29, 2006 in corresponding International Patent Application Serial No. PCT/US05/23200 (7 pages).
International Preliminary Report on Patentability dated Mar. 1, 2007 in corresponding International Patent Application No. PCT/US2005/030120 (6 pages).
Bale, MD, Reto J., et al, "Osteochondral Lesions of the Talus: Computer=assisted Retrograde Drilling Feasibility and Accuracy in Initial Experriences[1]", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug. 2001):pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A List of indications and realistic expectations", Foot and Ankle Surgery 1996 2:189-193, © 1996 Arnette Blackwell SA.
Taranow WS, et al, "Retrograde drilling of the osteochondral lesions of the medial talar dome", PubMed, www.pubmed.gov, A service of the National Library of Medicing and the Natinal Institutes of Health, Foot Ankle Int.Aug. 1999; 20(8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan. 2004): pp. 73-78.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.

Canadian Office Action dated Jan. 2, 2008 issued in corresponding Canadian Application No. 2407440.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Aug. 30, 2006 issued in corresponding PCT patent application No. PCT/US06/06323.
International Search Report and Written Opinion dated Nov. 27, 2006 issued in corresponding PCT patent application No. PCT/US06/00380.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Office Action issued in corresponding U.S. Appl. No. 10/741,044 dated Oct. 26, 2005.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Search Report in related EPO Application No. 03 02 6286.9 dated Feb. 26, 2004 (5pgs).
EPO Office Action dated Sep. 22, 2005 issued in corresponding European application 01932833.-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.

International Search Report and Written Opinion dated Oct. 1, 2008 issued in related International Patent Application No. PCT/US08/53194.

International Search Report and Written Opinion dated Oct. 9, 2008 issued in related International Patent Application No. PCT/US07/82262.

European Search Report dated Nov. 4, 2008 issued in related European Patent Application No. 04811836.8-2310.

Habermeyer, "Eclipse, Schaftfreie Schulterprothese Operationsanleitung," (dated unknown).

U.S. Office Action dated Jan. 9, 2009 issued in related U.S. Appl. No. 10/373,463.

Canadian Office Action dated Dec. 9, 2008 issued in related Canadian Patent Application No. 2407440.

Supplemental European Search Report dated Nov. 6, 2008 issued in related European Patent Application No. 05791453.3-2310.

Japanese Office Action dated Dec. 19, 2008 issued in Japanese Patent Application No. 2006501193.

Japanese Office Action dated Jan. 13, 2009 issued in Japanese Patent Application No. 2003552147.

International Search Report dated Jan. 30, 2006 issued in related International Patent Application No. PCT/US04/39181.

U.S. Office Action dated Mar. 27, 2009 issued in related U.S. Appl. No. 11/169,326.

European Office Action dated Feb. 26, 2009 in related European Patent Application No. 05791453.3.

McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Arthroplasty," Foot Ankle Clin. N. Am. 14 (2009) pp. 33-42.

Cook, et al., "Meta-analysis of First Metatarsophalangeal Joint Implant Arthroplasty," Journal of Foot and Ankle Surgery, vol. 48, Issue 2, pp. 180-190 (2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1): 56-63.

United States Office Action dated May 13, 2009 issued in related U.S. Appl. No. 11/359,892.

United States Office Action dated May 18, 2009 issued in related U.S. Appl. No. 11/209,170.

United States Office Action dated May 1, 2009 issued in related U.S. Appl. No. 11/461,240.

Australian Office Action dated Jan. 29, 2009 issued in related Australian Patent Application No. 2004216106.

European Search Report dated Apr. 22, 2009 issued in related European Patent Application No. 09002088.4.

U.S. Office Action dated Aug. 30, 2006 issued in related U.S. Appl. No. 10/618,887.

U.S. Office Action dated Jan. 15, 2008 issued in related U.S. Appl. No. 10/618,887.

U.S. Office Action dated May 18, 2009 issued in related U.S. Appl. No. 11/209,170.

U.S. Office Action dated May 28, 2009 issued in related U.S. Appl. No. 11/359,891.

U.S. Office Action dated May 13, 2009 issued in related U.S. Appl. No. 11/359,892.

International Search Report and Written Opinion dated Jun. 1, 2009 issued in related International Patent Application No. PCT/US2009/035889.

International Preliminary Report and Patentability dated May 7, 2009 issued in related International Patent Application No. PCT/US2007/082262.

Supplemental European Search Report dated May 28, 2009 issued in related International European Patent Application No. 01997077.1.

Supplemental European Search Report dated May 11, 2009 issued in related International European Patent Application No. 02805182.9.

Notice of Allowance dated Feb. 20, 2009 issued in related U.S. Appl. No. 10/618,887.

U.S. Office Action issued in related U.S. Appl. No. 11/326,133 dated Jun. 12, 2008.

International Search Report and Written Opinion dated Jun. 24, 2008 issued in related International Patent Application No. PCT/US07/73685.

International Search Report and Written Opinion dated Jun. 11, 2008 issued in related International Patent Application No. PCT/US07/25284.

International Search Report and Written Opinion dated Aug. 8, 2008 issued in related International Patent Application No. PCT/US08/53988.

Canadian Office Action issued in related Canadian Patent Application No. 2546582 dated Aug. 21, 2008.

Japanese Office Action dated Jul. 22, 2008 issued in related Japanese Patent Application No. 2006-501193.

U.S. Office Action issued in related U.S. Appl. No. 10/373,463 dated Apr. 21, 2008.

Notice of Allowance in U.S. Appl. No. 10/618,887 dated Aug. 15, 2008.

Australia Office Action issued in related Australian Patent Application No. 2007216648 dated May 30, 2008.

European Office Action issued in related European Patent Application No. 01932833.5-2310 dated Apr. 25, 2008.

U.S. Office Action in related U.S. Appl. No. 11/169,326 dated Jun. 30, 2008.

U.S. Office Action in related U.S. Appl. No. 11/169,326 dated Jul. 27, 2007.

U.S. Office Action in related U.S. Appl. No. 11/169,326 dated Apr. 17, 2007.

U.S. Office Action in related U.S. Appl. No. 11/169,326 dated Mar. 9, 2007.

Notice of Reasons for Rejection issued in related Japanese Patent Application No. 2003-394702 mailed Jul. 21, 2009.

Notice of Reasons for Rejection issued in related Japanese Patent Application No. 20-541615 mailed May 26, 2009.

International Preliminary Report on Patentability issued in related International Patent Application No. PCT/US2007/025284 dated Jun. 25, 2009.

Office Action issued in related Australian Patent Application No. 2007216648 dated Jul. 28, 2009.

European Search Report dated Jul. 10, 2009 issued in related European Patent Application No. 09002088.4.

Thermann, et al, ATOS Newsletter, Jun. 2005, Aktuelle Themen, (16 pages).

Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages), 2007.
APTA | Knee,/http://www.apta.org/AM/PrinerTemplate.cfm?Section=Home&TEMPLATE=/CM/HTMLDisplay.dfg&... Jun. 25, 2007 (1page).
Arthrosurface, Restoring the Geometry of Motion, HemiCAP Patello—Femoral Resurfacing System (19 pages), 2007.
Anatomical Arthroplastie, Total Evolutive Shoulder System T.E.S.S., Biomet France, Biomet Europe (4 pages), 2007.
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29& printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages), 2007.
Makita Industrial Power Tools, Product Details Print Out, Chain Mortiser, http://www.makita.com/menu.php?pg=product_det_prn& tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon& printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages), 2007.
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Japanese Notice of Reasons for Rejection dated Sep. 8, 2009 issued in related Japanese Patent Application No. 2003552147.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Reasons for Rejection dated Nov. 17, 2009 issued in Japanese Patent Application No. 2007-519417.
European Search Report dated Dec. 3, 2009 issued in related European Patent Application No. 06735827.5.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Preliminary Report on Patentaility dated Sep. 16, 2010 issued in related international Patent Application No. PCT/US2009/035889.
Supplemental Notice of Allowance dated Oct. 6, 2010 issued in related U.S. Appl. No. 12/415,503.
Office Action dated Sep. 21, 2010 issued in related U.S. Appl. No. 11/169,326.
Office Action dated Sep. 29, 2010 issued in related U.S. Appl. No. 11/461,240.
International Preliminary Report on Patentability dated Sep. 16, 2010 issued in related International Patent Application No. PCT/US2009/035889.
Office Action dated Oct. 11, 2010 issued in related Australian Patent Application No. 2006216725.

* cited by examiner

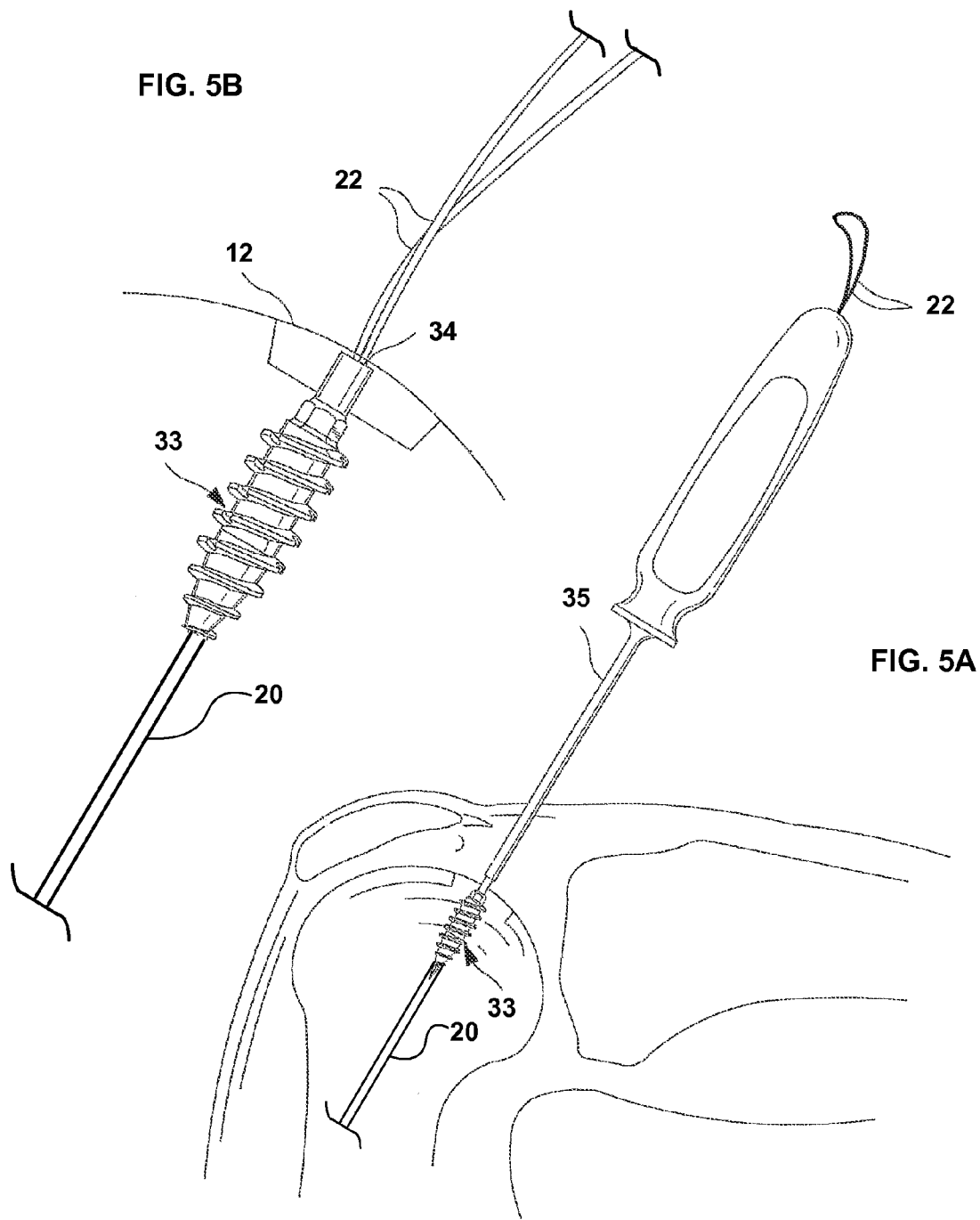

RETROGRADE DELIVERY OF RESURFACING DEVICES

CROSS-REFERENCE TO RELATED APPLICATION

This application claims the benefit of U.S. provisional patent application Ser. No. 60/523,810, filed on Nov. 20, 2003, and is a continuation-in-part of U.S. patent application Ser. No. 10/308,718, filed on Dec. 3, 2002 now U.S. Pat. No. 7,163,541, the entire disclosure of which is incorporated herein by reference.

FIELD

The present disclosure is directed at a system and method of repairing a defect in an articular joint surface.

BACKGROUND

Articular cartilage, found at the ends of articulating bone in the body, is typically composed of hyaline cartilage, which has many unique properties that allow it to function effectively as a smooth and lubricious load bearing surface. Hyaline cartilage problems, particularly in knee, hip joints, and should joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and eventually, loss of joint movement. As a result, various methods have been developed to treat and repair damaged or destroyed articular cartilage.

For smaller defects, traditional options for this type of problem include leaving the lesions or injury alone and living with it, or performing a procedure called abrasion arthroplasty or abrasion chondralplasty. The principle behind this procedure is to attempt to stimulate natural healing. The bone surface is drilled using a high speed rotary burr or shaving device and the surgeon removes about 1 mm of bone from the surface of the lesion. This creates an exposed subchondral bone bed that will bleed and will initiate a fibrocartilage healing response. One problem with this procedure is that the exposed bone is not as smooth as it originally was following the drilling and burring which tends to leave a series of ridges and valleys, affecting the durability of the fibrocartilage response. Further, although this procedure can provide good short term results, (1-3 years), fibrocartilage is seldom able to support long-term weight bearing and is prone to wear, soften and deteriorate.

Another procedure, called Microfracture incorporates some of the principles of drilling, abrasion and chondralplasty. During the procedure, the calcified cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique may be expected to be similar to abrasion chondralplasty.

Another means used to treat damaged articular cartilage is a cartilage transplant. Essentially, this procedure involves moving cartilage from an outside source or other knee or from within the same knee into the defect. Typically, this is done by transferring a peg of cartilage with underlying bone and fixing it in place with a screw or pin or by a press fit. Although useful for smaller defects, large defects present a problem, as this procedure requires donor pegs proportionate to the recipient bed. Large diameter lesions may exceed the capacity to borrow from within the same knee joint and rule out borrowing from another source.

Larger defects, however, generally require a more aggressive intervention. Typically treatment requires replacing a portion or all of the articular surface with an implant or prosthetic having an outer layer that that is polished or composed of a material that provides a lubricious load bearing surface in approximation of an undamaged cartilage surface. Replacement of a portion, or all, of the articular surface requires first cutting, boring, or reaming the damaged area to remove the damaged cartilage. A recess to receive an implant or prosthetic is formed at the damaged site. The implant or prosthetic is then secured to the bone in an appropriate position in the recess.

The treatment and/or replacement procedure often requires direct access to the damaged surface of the cartilage. While the most commonly damaged portions of some joints may easily be accessed for repair using a minimally invasive procedure some joints are not nearly as accessible. For example, the superior or medial femoral head, the medial humeral head, the glenoid, etc. do not permit direct access sufficient to carry out replacement of the articular surface in a minimally invasive manner. In fact, repair of such obstructed joints often requires an invasive procedure and necessitates complete dislocation of the joint. Procedures of such an invasive nature may be painful and require an extended recovery period.

BRIEF DESCRIPTION OF THE DRAWINGS

Features and advantages of the claimed subject matter will be apparent from the following detailed description of exemplary embodiments consistent therewith, which description should be considered in conjunction with the accompanying drawings, wherein:

FIG. 5A is a sectional view of an exemplary fixation screw consistent with one embodiment of the present disclosure; and FIG. 5B is a side partial cross-sectional view of the exemplary fixation screw of FIG. 5A, implanted in the defect, with suture strands placed therethrough, in a surgical procedure consistent with one embodiment of the present disclosure.

DETAILED DESCRIPTION

As a general overview, the present disclosure may provide a system and method for replacing at least a portion of an articular surface of a joint. The present disclosure may allow instruments and/or other devices to be delivered to a target area, e.g. an articular surface or portion thereof, within a joint. According to one aspect, the present disclosure may allow instruments and/or other devices to be delivered to a target area that is obscured from direct frontal or axial access. Furthermore, consistent with the system and method herein, the instruments and/or devices delivered to the target area may be used to perform a diagnostic and/or therapeutic procedure on a target area obscured from direct frontal or axial access. According to one embodiment, a method is provided for repairing a defect in an articular surface of a joint. The method herein may be useful, for example, for repairing defects on portions of an articular surface of a joint that are obstructed from direct access by mating joint surfaces and/or other anatomical features. Such obstructed articular surfaces may be accessed and/or repaired without requiring complete dislocation of the joint. Accordingly, the present disclosure may provide a less invasive system and method for repairing an articular joint surface.

Embodiments of the present disclosure are described in the context of repairing a region of the articular surface of a femoral head. Specifically, the illustrated and described embodiment is directed at the retrograde access, implant site preparation, and delivery of a prosthetic resurfacing device to the femoral head. Those having skill in the art will appreciate, however, that the principles herein may be utilized for accessing target areas other than the femoral head and may be used in connection with procedures other than prosthetic resurfacing of an articular surface. Without intending to limit the claimed subject, in addition to providing retrograde delivery of implants, diagnostic devices, surgical instruments, etc., to the superior or medial femoral head, the method herein is equally suitable for retrograde delivery to sites such as, cut not limited to, the medial humeral head, tibial surface and patella. Similarly, the method herein may be used for thru-bone delivery of prosthetic implants, diagnostic devices, surgical instruments devices, etc. to sites such as the glenoid, acetabulum, trochlear groove, etc.

Figure 1:
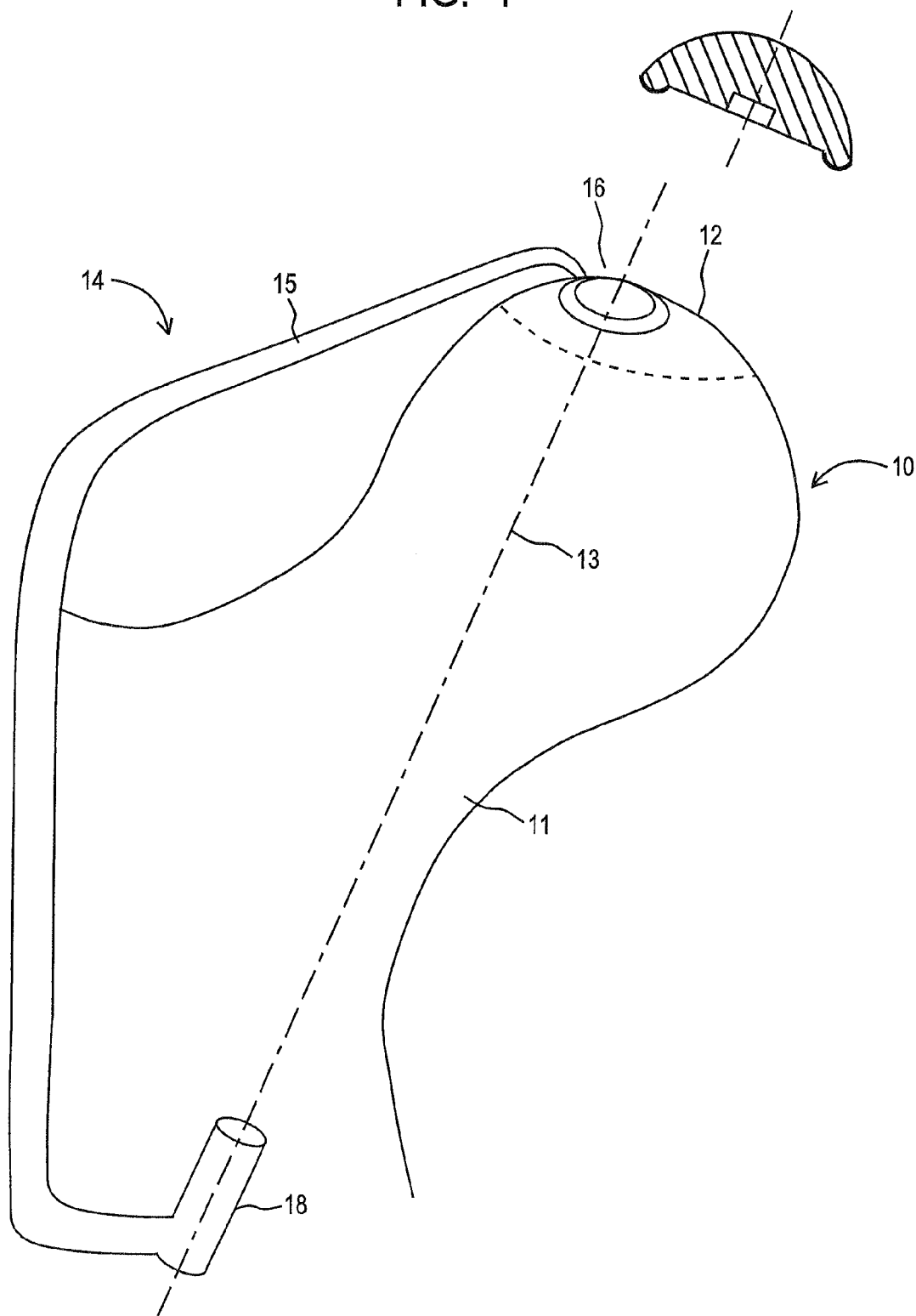
FIG. 1 depicts a femoral head having a target site for receiving a prosthetic implant.

Referring to FIG. 1, the system is depicted with reference to a femoral head 10. A region of the articular surface of the femoral head 10 to be replaced, i.e., the target area 12, is indicated by broken lines. According to one embodiment, a method herein may include drilling a passage along a predetermined working axis 13 through the femur 11 towards the target area 12 on the femoral head 10. The passage through the femur 11 may provide access to the target area 12 of the femoral head 10. In the case of the illustrated embodiment, the origin of the drill site may be on the body of neck of the femur 11 directed toward the target area 12 on the femoral head 10.

The passage through the femur 11 may be oriented generally normal to the articular surface of the femoral head 10 in the vicinity of the target area 12. As shown in FIG. 1, a drill guide 14 may be used to orient an access passage generally normal to the target area 12 of the articular surface of the femoral head 10. The drill guide 14 may include a locating ring 16 and a drill bushing 18. The drill bushing 18 may be connected to the locating ring 16 by an arm 15 of the drill guide 14. The arm 15 of the drill guide 14 may orient the drill bushing 18 in a generally coaxial relationship relative to the locating ring 16 along the working axis 13. As depicted, the locating ring 16 may include a generally annular member. As such, when the locating ring 16 is disposed on the arcuate surface of the femoral head 10, the locating ring 16 may attain an orientation generally normal to the surface of the femoral head 10. The coaxial orientation of the drill bushing 18 and the locating ring 16 may allow a passage to be drilled through the femoral head 10, and guided by the drill bushing 18, to be substantially normal to the articular surface of the femoral head 10 at the target area 12. Consistent with the present disclosure, a drill axis defined by the drill bushing 18 may have an orientation that is not normal to the femoral head 10 in the target area 12.

Figure 2:
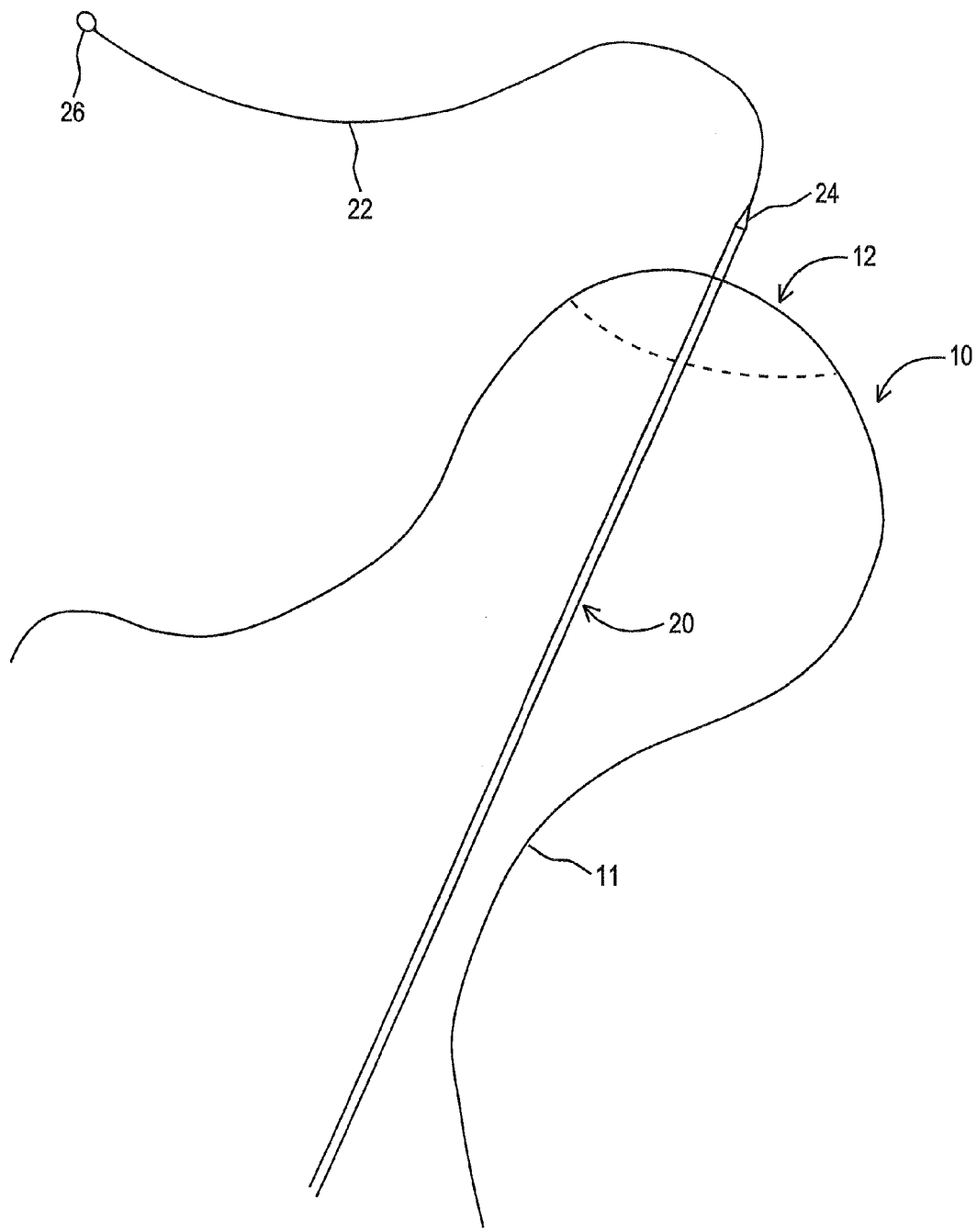
FIG. 2 illustrated the formal head of FIG. 1 having a passage drilled there-through consistent with the present disclosure.

Turning to FIG. 2, a passage 20 is shown provided through the femur 11, extending trough the femoral head 10 in the region of the target area 12. As discussed above, the passage 20 may be formed by drilling through the femur 11 using a drill bit guided by the drill bushing 18 of the drill guide 14. A tether 22, such as a wire, suture, thread, etc., may be inserted through the passage 20 so that the tether 22 may extend from the femoral head 10. The tether 22 may be advanced though the passage 20 with the aid of a guide pin 24. For example, the guide pin 24 may be a cannulated rod and the tether 22 may be at least partially disposed in a lumen of the guide pin 24. According to an alternative embodiment, the guide pin 24 may simply be a rod that may be used to push, or otherwise advance, the tether 22 through the passage 20. As shown, the tether 22 may include a loop 26 on the distal end thereof. The loop 26 or feature may be used for attaching instruments, devices, etc., to the tether 22. Accordingly, various attachment features other than a loop may suitably be employed herein.

Figure 3:
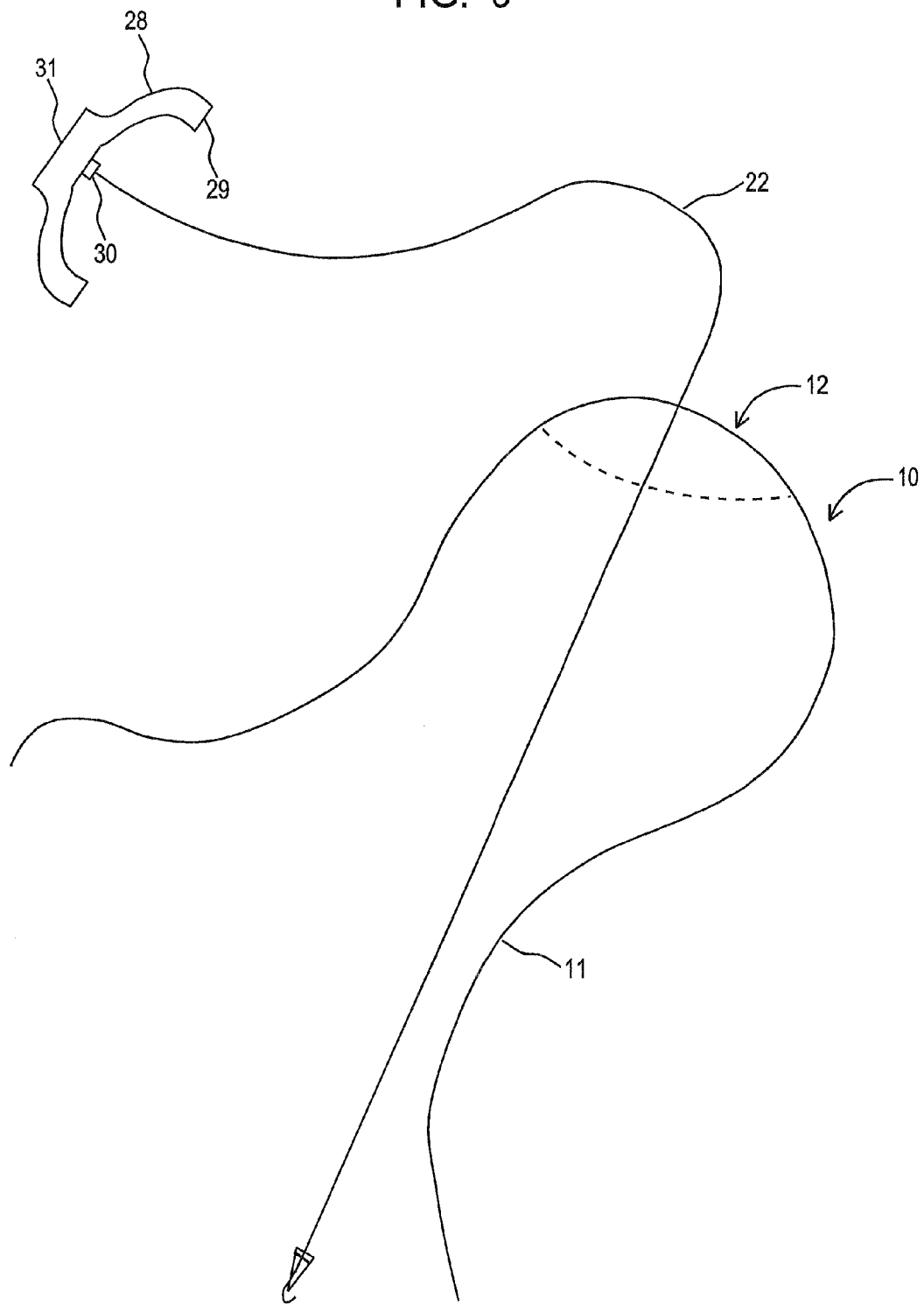
FIG. 3 shows the use of a wire inserted through the femoral head shuttling devices to the target area.

The tether 22 may be used to ferry, shuttle, or otherwise convey various diagnostic devices, surgical instruments, prosthetic devices, etc. from a remote insertion site, e.g., exterior to the joint, to the target area 12. In one embodiment, the tether 22 may be used to convey instruments, devices, etc., to the target area 12 without requiring direct and/or axial access to the target area 12. For example, referring the FIG. 3, the tether 22 may be coupled to a reamer 28 outside of the joint. The reamer 28 may include a body 31 and one or more cutting features 29 and may be used for excising a portion of the femoral head 10 in the region of the target area 12. The tether 22 may be advanced or pulled through the femur 11 and out from the joint area to allow the reamer 28 to be attached to the tether 22 at the remote insertion site. Advancing the tether 22 from femoral head 10 may include pulling the distal end of the tether 22 completely from the body of a patient, e.g., in an embodiment in which the remote insertion site it outside of the patient. The loop 26 at the distal end of the tether 22 may be coupled to a cooperating feature 30 on an underside of the reamer 28. The reamer 28 may be conveyed to the target area 12 by withdrawing the tether 22 back through the passage 20, thereby pulling and or guiding the reamer 28 to the target area 12. Withdrawing the tether 22 back through the passage 20 may transport the reamer 28 to the target area 12 and/or may generally center the attachment feature 30 of the reamer 28 relative to the passage 20.

Figure 4:
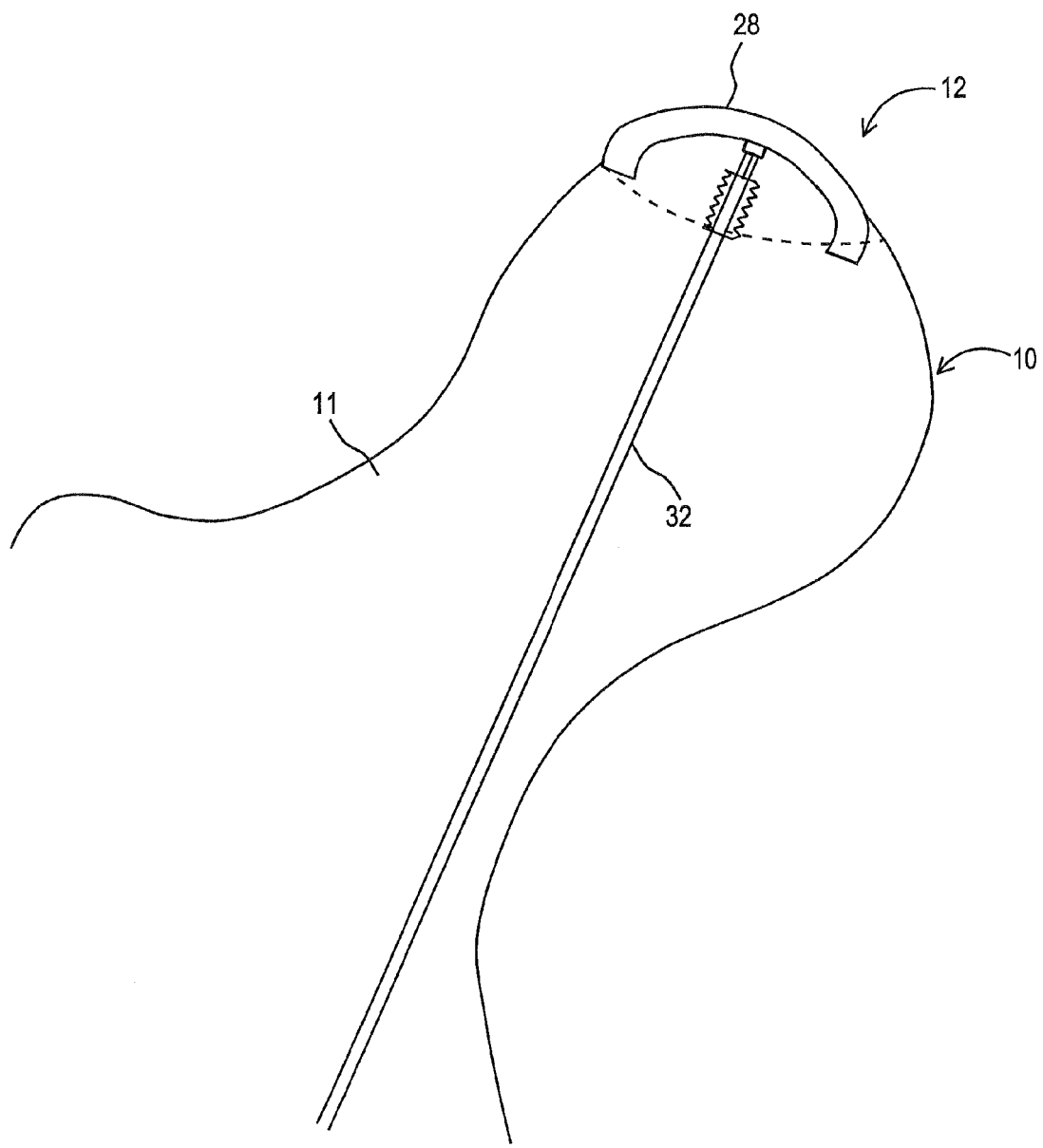
FIG. 4 depicts a reamer employed via a drive shaft extending through the passage in the femoral head.

Turning to FIG. 4, once the reamer 28 has been transported to the target area 12, the reamer 28 may be coupled to a drive shaft 32 disposed extending at least partially through the passage 20. In one embodiment, the drive shaft 32 may be a cannulated shaft that may be threaded over the tether 22. The reamer 28 and the drive shaft 32 may include cooperating features allowing the driveshaft 32 to transmit torque to the reamer 28. The cooperating features of the drive shaft 32 and the reamer 28 may include torque transmitting features such as cooperating a cooperating socket and plug, e.g., a mating hex shaft and hex socket. Consistent this variety of torque transmitting coupling the wire 22 may be used to pull the reamer 28 towards in the drive shaft 32 in order to maintain the connection between the cooperating features of the drive shaft 32 and the reamer 28. Alternatively, the cooperating features of the drive shaft 32 and the reamer may be releasably securable to one another. According to one such embodiment, the cooperating features of the drive shaft 32 and the reamer 28 may include cooperating threaded components that screw together, cooperating snap-fit features, etc.

At least a portion of the femoral head 10 in the general region of the target area 12 may be excised by rotatably driving the reamer 28 and pulling the reamer 28 into the femoral head 10. The reamer 28 may be rotatably driven manually and/or using a drive motor, for example using a drill. The reamer 28 may be pulled into the femoral head 10 by withdrawing the drive shaft 32, in an embodiment in which the drive shaft 32 and the reamer 28 are releasably secured to one another. Additionally, and/or alternatively, the reamer 28 may be pulled into the femoral head by withdrawing or pulling on the tether 22, which may, in some embodiments, remain coupled to the reamer 28 during the excision operation.

In addition to conveying the reamer 28 to the target area 12, the tether 22 may also be used to transport various other devices and/or instruments to the target area 12. Devices and/or instruments transported to the target area 12 by the tether 22 may also be centered about the passage 20 through the femur 11 similar to the reamer 28. For example, in an embodiment consistent with the present disclosure, also in the general context of an articular surface repair procedure, the tether 22 may be used to shuttle or transport an anchoring device, such as a screw 33, FIGS. 5A and 5B, to the target area 12. The screw 33 may be provided having an internal driving feature 34, e.g., a hex socket feature, a Torx™ socket, etc. The tether 22 may be threaded through a cannulated driver 35 which may be inserted through the passage 20. The tether 22 may be used to convey the screw 33 to the target area 12 and center the screw 33 relative to the passage 20. The driver 35 may be engaged with the driving feature 34 of the screw 33 and a holding force may be applied to the screw 33 via the tether 22, thereby maintaining the engagement between the driver 34 and the screw 33. With the driver 34 and the screw 33 maintained in engagement with one another, the screw 33 may be threadably driven into the passage 20 at the target area 12.

In a related manner, the tether 22, alone and/or in conjunction with various suitably configured shafts and/or driving elements extending through the passage 20, may be used to transport and operate or install other instruments and devices. Ultimately, the tether 22 may be used to shuttle a prosthetic implant to the target area 12 and install the implant into an implant site, such as may be created using the reamer 28.

Consistent with the foregoing disclosure, a system and method may be provided for replacing at least a portion of an articular surface of a joint that is obscured from axial approach. According to one aspect, a method herein may permit the retrograde delivery of instruments and devices from an insertion site to a target area on the articular surface. According to an embodiment, the method may include drilling a passage from an accessible region of a bone removed from a target articular surface. The passage may extend toward the target articular surface. A tether, such as a wire, may be introduced through the passage, and positioned having a distal end extending from a distal opening of the passage at the target articular surface. The distal end of the tether may be coupled to a prosthetic device, a surgical instrument, diagnostic device, etc. The tether may then be drawn back toward the articular surface, thereby transporting/carrying the prosthetic device, surgical instrument, diagnostic device, etc. to the articular surface.

According to another aspect, after the a prosthetic device, surgical instrument, diagnostic device, etc., has been transported to the articular surface, the prosthetic device, surgical instrument, diagnostic device, etc. may be engaged by a shaft or pin extending through said passage to said articular surface. The shaft or pin may be used for applying a rotational and/or axial force to the prosthetic device, surgical instrument, diagnostic device, etc. Using this methodology, a procedure may be performed on a target are without direct axial or frontal access to the target area.

Those having skill in the art will appreciate that the method herein may be used for transporting numerous additional instruments, devices, etc. to a working surface having impeded direct axis. Further is should be understood that a variety of pins, shafts, catheters, etc. may be inserted through the passage for acting on, interacting with, or co-acting with instruments and/or devices transported to a target area consistent with above aspects of the disclosure. Finally, it should also be understood that the embodiments disclosed herein are susceptible for use in procedures in addition to the repair of articular cartilage at a joint. Accordingly, it should be understood that the embodiments that have been described herein are but some of the several contemplated within the scope of the claimed subject matter, and are set forth here by way of illustration, but not of limitation. It is obvious that many other embodiments, which will be readily apparent to those skilled in the art may be made without departing materially from the spirit and scope of the claimed subject matter.

What is claimed is:

1. A system for creating an implant site on an articular surface of a bone comprising:
   a drill guide comprising:
      an annular locating ring configured to be disposed generally normal to said articular surface and at least partially about a defect on said articular surface;
      a drill bushing defining a working axis extending through said annular locating ring; and
      an arm co-axially aligning said locating ring and said drill bushing;
   a drill bit configured to be received at least partially through said drill bushing along said working axis to drill a passage through said bone substantially normal to said articular surface and provide an opening on said articular surface about said defect;
   a shuttle configured to be at least partially disposed within said passage in said bone, said shuttle further configured to be coupled to a device and to deliver said device to said working axis;
   a reamer configured to excise an implant site in a portion of said articular surface about said defect, said reamer further configured to be coupled to said shuttle and configured to be conveyed to said articular surface by said shuttle;
   a cannulated drive shaft configured to be at least partially disposed within said passage and further configured to be coupled to said reamer, wherein said shuttle is configured to be at least partially disposed within a lumen of said cannulated shaft and is further configured to be secured to said reamer;
   a screw configured to be coupled to said shuttle and configured to be conveyed to said implant site and center said screw with respect to said implant site; and
   a driver configured to engage said screw to threadably drive said screw into said passage.

2. A system according to claim 1, wherein said arm of said drill guide orients said locating ring and said drill bushing in a coaxial relationship.

3. A system according to claim 1, wherein a distal end of said shuttle comprises an attachment mechanism configured to be coupled to said device for conveying said device to said articular surface.

4. A system according to claim 1, where said reamer is configured to be conveyed to said articular surface by coupling said reamer to said shuttle and withdrawing said shuttle through said passage drilled through said bone.

5. A system according to claim 1 wherein said arm is configured to orientate said locating ring generally at an angle other than normal to said articular surface.

6. A system according to claim 1 wherein said shuttle comprises a tether.

7. A system according to claim 6 wherein said tether comprises a wire.

8. A system according to claim 6 wherein said tether comprises a suture.

9. A system according to claim 6 wherein said tether comprises a thread.

10. A system according to claim 6 further comprising a guide pin configured to be at least partially disposed within said passage.

11. A system according to claim 10 wherein said guide pin comprises a rod.

12. A system according to claim 11 wherein said guide pin comprises a cannulated rod.

13. A system according to claim 12 wherein said tether is configured to be at least partially disposed in a lumen of said guide pin.

14. A system according to claim 1, wherein said drive shaft and said reamer each comprise a cooperating threaded component.

15. A system according to claim 1, wherein said drive shaft and said reamer each comprise a cooperating torque transmitting feature.

16. A system according to claim 15 wherein said cooperating torque transmitting features comprise a cooperating socket and plug.

17. A system according to claim 1, wherein said drive shaft and said reamer are releasably securable.

18. A system according to claim 3 wherein said attachment mechanism comprises a loop.

* * * * *